United States Patent [19]

Hannam et al.

[11] 4,354,042
[45] Oct. 12, 1982

[54] PROCESS FOR MAKING N,N,N',N'-TETRAACETYLETHYLENEDIAMINE

[75] Inventors: Stephen J. Hannam, Clwyd, Wales; John S. Saynor; Anthony D. Watling, both of Leeds, England

[73] Assignee: Warwick Chemical Limited, Leeds, England

[21] Appl. No.: 214,404

[22] Filed: Dec. 8, 1980

[30] Foreign Application Priority Data

Jun. 27, 1980 [GB] United Kingdom ............... 8021142

[51] Int. Cl.$^3$ .......................................... C07C 102/00
[52] U.S. Cl. .................................. 564/144; 564/133
[58] Field of Search .............................. 564/144, 133

[56] References Cited

U.S. PATENT DOCUMENTS 3,223,732 12/1965 Viveen et al. ..................... 564/144
3,824,286 7/1974 Grimmelikhuysen et al. .. 564/144 X
3,824,287 7/1974 Ludwigshafen et al. ............ 564/144

FOREIGN PATENT DOCUMENTS 4919 10/1979 European Pat. Off. ............ 564/144
907357 10/1962 United Kingdom ................ 564/144
1335204 10/1973 United Kingdom ................ 564/144
1378308 12/1974 United Kingdom ................ 564/144
191560 3/1967 U.S.S.R. ............................. 564/144

Primary Examiner—John Doll
Attorney, Agent, or Firm—Lawrence Rosen

[57] ABSTRACT

N,N,N',N'-tetraacetylethylenediamine (TAED) is made by an improved multicyclic process, which comprises, in each cycle, the steps of reacting N,N'-diacetylethylenediamine (DAED) with acetic anhydride and thereby forming a reaction mixture of N,N,N',N'-tetraacetylethylenediamine and acetic acid and anhydride, and distilling off acetic acid and working up the distillation residue to give substantially pure N,N,N',N'-tetraacetylethylenediamine, and in which the molar ratio of DAED:acetic anhydride in each cycle is at least 1:6.

17 Claims, No Drawings

PROCESS FOR MAKING N,N,N',N'-TETRAACETYLETHYLENEDIAMINE

This invention relates to processes for the production of TAED, which is an important auxiliary agent for use in detergents and similar compositions, where it acts as a perborate activator. In this specification TAED stands for N,N,N',N'-tetraacetylethylenediamine, DAED stands for N,N'-diacetylethylenediamine and EDA stands for ethylenediamine.

It is known to make TAED by reaction of DAED and excess acetic anhydride followed by distillation of acetic acid from the reaction mixture and separation of acetic anhydride from the TAED. It is known that this can be conducted as a cyclic process with the acetic anhydride separated in one cycle being used as a feed stock in another cycle.

The process involves an equilibrium reaction and the presence of acetic acid in the starting materials tends to suppress the yield. Unfortunately the separated acetic anhydride is contaminated with acetic acid and so yields tend to be low when using the anhydride for successive cycle. Attempts to remove all the acid results in the formation of coloured impurities and this is unacceptable. Examples are described in British patent specification No. 1,378,308 and European patent specification No. 4919.

DAED can be made by reaction of EDA with acetic acid, for instance as described in Journal Chem. Education 14, 141-2, 1939 or British specification No. 1,335,204.

A multi-cyclic process according to the invention for making TAED comprises, in each cycle, the step of reacting DAED with acetic anhydride, part at least of which is recovered from another cycle, and thereby forming a reaction mixture of TAED and acetic acid and anhydride and then distilling off acetic acid and anhydride and working up the distillation residue to give substantially pure TAED, and in this process we use one or more of the following steps:

(1) the molar ratio of DAED:acetic anhydride in this step in each cycle is at least 1:6;

(2) the total volume, per unit volume of reaction mixture in this step, of distillate distilled from the reaction mixture in one cycle is more than the total volume, per unit volume of reaction mixture in this step, distilled from the reaction mixture in a preceding cycle;

(3) the working up of the distillation residue comprises recrystallisation of TAED from acetic anhydride and the recrystallisation liquors are recycled for the reaction with DAED.

Preferably the process is carried out using steps (1) and (2) or steps (1), (2) and (3), but it may also be carried out using for instance steps (1) and (3) or steps (2) and (3) or any individual step.

Each of the steps gives a surprising increase in yield based on EDA and improved utilisation of acetic anhydride without impairment of the purity of the TAED produced. For instance step (1) gives a very large increase compared to processes in which the molar ratio is not strictly controlled at a figure above 1:6 in each cycle.

The recrystallisation liquors contain for instance 7 to 10% acetic acid and impurities from the recrystallisation process and also a small amount of TAED and the trisubstituted compound. In British specification 1,378,308 it is suggested that up to 5% acid based on TAED can be tolerated but we surprisingly find that 10% based on anhydride (about 70% based on DAED) can be recycled and good yield and quality obtained, especially when conducted with steps (1) and/or (2).

It is very surprising that these various steps individually and collectively can be used so as to push the yield based on raw materials to very near the optimum and yet still obtain a product that is substantially pure, since in the published prior art it has been well recognised that high conversions tend to result in serious impurity problems with the result that steps are deliberately taken to keep conversions low. In the invention however we obtain high conversion of EDA and use of anhydride and still obtain a pure product as a result of the various features described.

The invention is normally carried out as part of a cyclic multistep process for making TAED in which each cycle comprises reacting EDA with acetic acid to form DAED and reacting substantially all the DAED with acetic anhydride recovered from another cycle and thereby forming reaction mixture comprising TAED and acetic acid and anhydride.

The acetic anhydride that is recovered from another cycle is generally acetic anhydride that is recovered during the working up of the distillation residue resulting from distilling acetic acid from the reaction mixture of TAED and acetic acid and anhydride. The working up may comprise phase separation, generally accompanied by cooling, of TAED from the distillation residue or other liquors containing acetic anhydride, reslurrying of TAED with acetic anhydride generally followed by phase separation, or recrystallisation of TAED from acetic anhydride and generally a combination of all three procedures is used. The liquor resulting from one or more of these procedures is recycled. Generally the working up comprises phase separation and reslurrying and these liquors are combined and recycled. When the working up includes recrystallisation as described these liquors may be recycled, as in step (3).

Conveniently the process is carried out in at least two and usually three or more cycles with the liquors from the working up steps in the one cycle being used for reaction with the DAED in the next cycle and with the liquors from the working up steps in the next cycle being used for reaction with the DAED in the final cycle. Although the recrystallisation liquors from the final cycle can be recycled for reaction with DAED, for instance in the first cycle of another process, the other acetic anhydride containing liquors from the final cycle are generally run to waste.

The reaction between EDA and acetic acid may be conducted in the presence of acetic anhydride and is preferably conducted by mixing acetic acid and EDA, allowing the temperature to rise and distilling off the water of reaction and acetic acid, usually with additional heating.

The reaction between DAED and acetic anhydride is best conducted by heating at 120° to 170° C. for 15 minutes to three hours accompanied by distillation of acetic acid from the reaction mixture. The distillation is preferably conducted until near the time when coloured by-products are formed. The amount of distillate removed is usually between 15 and 40% by volume, preferably about 25% by volume, based on the amount of acetic anhydride added to the DAED. The preferred reaction and distillation temperature is from 140° to 150° C.

There is described in copending application Ser. No. 214,403 filed even date herewith by Stephen John Hannam processes including, inter alia, a multicyclic process for making TAED in which each cycle comprises (a) reacting DAED in a vessel with acetic anhydride part at least of which is recovered from another cycle and thereby forming the reaction mixture comprising TAED and acetic acid and acetic anhydride, (b) distilling the reaction mixture to remove acetic acid from the mixture and (c) working up the distillation residue to give substantially pure TAED, and in which in step (b) further acetic anhydride is added to the mixture before the distillation of the acetic acid is complete and distillation of acetic acid is thereafter continued. The disclosure of this application is hereby incorporated by reference. The process of the present invention is preferably operated in conjunction with the process described in that application. In particular the distillation in step (b) is preferably conducted by distilling some acetic acid from the reaction mixture, subsequently adding acetic anhydride to the reaction mixture, and subsequently distilling further acetic acid from the mixture. Generally this is achieved by distilling acetic acid, adding an amount of acetic anhydride substantially the same as the amount of distillate that has been removed and then distilling further distillate, the amount generally being from 0.5 to 2.5, preferably 0.8 to 1.5, times the amount of distillate removed initially. In the final cycle the amount is usually 1.2 to 2 times the amount removed in the preceding cycle. The amount of distillate removed at each stage is generally between 15 and 40% by volume based on the amount of acetic anhydride added initially to the DAED.

The molar ratio of DAED:acetic anhydride in each cycle is preferably always at least 1:6.5 and generally at least 1:6.8. By having such a ratio in the first cycle and maintaining it in subsequent cycles improved utilisation of reactants is obtained without formation of impurities. The ratio is generally below 1:10, preferably below 1:7.5 or 1:7.2, with best results being obtained with a ratio of about 1:7.0. Normally the described step in each cycle is carried out using the same volume of reaction mixture in which event the amount of DAED introduced into that reaction mixture for reaction in each cycle should be less than in a preceding cycle, in order to maintain the ratio DAED:acetic anhydride substantially constant. When, as is normal, the reaction is conducted by reacting EDA with acetic acid and when, as is normal, the volume of reaction mixture in each cycle is constant the amount of EDA introduced in a subsequent cycle should be less than the amount introduced in a preceding cycle. Generally the amount introduced in second and subsequent cycles is between 30 and 90%, preferably 50 to 90% by weight of the amount introduced into the first cycle. The amount in third and any subsequent cycles may be the same as, but is generally less than (for instance being 50 to 90% by weight) of the amount used in the second cycle.

The volume of the TAED-acetic acid reaction mixture formed in each cycle is usually the same in which event the amount of distillate removed from the reaction in one cycle may be more than the amount removed in the preceding cycle. Preferably the amount is from 10 to 150% more than the amount removed in a preceding cycle. When each cycle is conducted with a single distillation stage only the amount in one cycle is generally from 10 to 60% more than the amount in the preceding cycle but when one stage is conducted with two distillation steps, as described above, and the preceding stage is conducted with a single distillation step then the total amount removed is generally from 50 to 150% more than the amount removed in the single step.

When TAED is purified by recrystallisation from acetic anhydride this is preferably effected by heating at 80° to 120° C., preferably about 100° C., for a period of 10 minutes to one hour followed by cooling and separation of the mother liquors from the TAED crystals. These mother liquors may also be recycled to the step in the next cycle in which DAED is reacted with acetic anhydride but preferably all the recrystallisation liquors from each cycle are recycled to the first cycle of a fresh cyclic multistep process.

The following are examples of the invention as applied to a three cycle process: Examples 1 and 2 are of laboratory processes while the other Examples are of industrial processes.

EXAMPLE 1

In the first cycle 60 g (1 M) EDA amine was reacted with 120 g (2.66 M) acetic acid and the mixture distilled and vacuum was then applied. After several minutes the head temperature started to drop and the distillation was terminated.

720 g (7.05 M) acetic anhydride was added and the mixture brought to reflux. A slow distillation at atmospheric pressure was carried out after 30 minutes refluxing. This was to remove the acetic acid formed in the reaction and was terminated on collecting 150 ML of distillate.

The solid formed on cooling was filtered off, washed with acetic anhydride and given one water slurry before drying. The yield was 129 grams which is a 56% yield based on EDA. The mother liquors separated by the filtration were used in the second cycle.

In the second cycle 33 g (0.55 M) EDA was reacted with 160 g acetic acid and the mix distilled as before and then the total mother liquors from the first cycle was added and the mixture refluxed, distilled, filtered to give a solid and mother liquors, the solid was washed with anhydride and the solid water slurried as before. The yield of TAED was 138.6 g.

In the third cycle the process described in the second cycle was repeated except that the amount of EDA used was 30 g (0.5 M). The yield was 134.4 g.

The total yield of TAED in the process is thus 402 g which is 86% overall of EDA.

EXAMPLE 2

As a comparison, the process of Example 1 was repeated but using the more normal procedure of using the same amount, 60 g EDA in each cycle. The total yield of TAED obtained is 410 g, which is 45% overall on EDA.

EXAMPLE 3

In the first cycle 600 kg EDA and 1500 liters acetic acid are mixed and heated to distillation. Acetic acid and water is distilled off until distillation ceases at a temperature of about 150° C. and then the last traces of acetic acid are stripped by vacuum. 7000 liters of fresh acetic anhydride are charged. The temperature is raised to 140° to 150° C. and a mixture of acetic acid and acetic anhydride is distilled off until 1400 liters have been removed. 1400 liters acetic anhydride are then added and a further 1400 liters acetic acid-anhydride mixture is distilled off. The batch is cooled to 30° C. and stood to settle out the TAED. The acetic anhydride mother liquor is filtered off and the TAED is washed with acetic anhydride and then with water and is then dried. In the second cycle the process is the same except that the 7000 liters of liquid charged to the DAED is made up of mother and anhydride wash liquors from the first cycle.

The third cycle is conducted in similar manner. The yield is approximately 58% based on EDA used.

EXAMPLE 4

The process of Example 3 is repeated except that a single distillation of 1500 liters is conducted in each cycle. The yield of TAED is 3100 kg based on 1800 kg EDA, namely 45%.

EXAMPLE 5

When the process of Example 4 is repeated but removing 1700 kg distillate in the first cycle, 1700 kg distillate in the second cycle and 2100 kg distillate in the third cycle. The yield of TAED is 3500 kg, namely 51% on EDA.

EXAMPLE 6

The process of Example 3 is repeated but 2100 kg distillate is removed in the final distillation in the final cycle, the amount of EDA in the second cycle is 500 kg and the amount in the final cycle is 400 kg and the washed solid TAED is recrystallised in each stage. Recrystallisation is by heating in acetic anhydride at 100° C. followed by cooling and filtering. The resultant mother liquors are all recycled for use as the source of acetic anhydride in the first cycle. The yield of TAED is above 65% based on EDA.

We claim:

1. A multicyclic process for making TAED which comprises, in each cycle, the step of reacting DAED with acetic anhydride, part at least of which is recovered from another cycle, and thereby forming a reaction mixture of TAED and acetic acid and anhydride and then distilling off acetic acid and working up the distillation residue to give substantially pure TAED, and in which the total volume, per unit volume of reaction mixture in this step, of distillate distilled from the reaction mixture in one cycle is more than the total volume, per unit volume of reaction mixture in this step, distilled from the reaction mixture in a preceding cycle.

2. A process according to claim 1 in which the volume of distillate distilled from the said reaction mixture in one cycle is from 10 to 150% more than the volume removed in a preceding cycle.

3. A process according to claim 1 in which each cycle is conducted with a single distillation stage and the volume removed in one cycle is from 10 to 60% more than the volume removed in the preceding cycle.

4. A process according to claim 1 in which in at least one cycle after the first cycle the distillation of acetic acid is conducted by distilling acetic acid, adding an amount of acetic anhydride substantially the same as the amount of distillate that has been removed and then distilling further distillate and in which the total volume of distillate removed in this process is 50 to 150% more than the volume removed in the distillation during a preceding cycle.

5. A multicyclic process for making TAED which comprises, in each cycle, the step of reacting DAED with acetic anhydride, part at least of which is recovered from another cycle, and thereby forming a reaction mixture of TAED and acetic acid and anhydride and then distilling off acetic acid and working up the distillation residue to give substantially pure TAED, and in which the working up of the distillation residue comprises recrystallisation of TAED from acetic anhydride and the recrystallisation liquors are recycled for the reaction with DAED.

6. A process according to claim 5 in which the working up of the distillation residue comprises at least one step selected from phase separation and cooling of the residue, reslurrying TAED with acetic anhydride followed by phase separation, and recrystallisation from acetic anhydride.

7. A process according to claim 5 in which liquors from the working up steps in one cycle are used for reaction with DAED in the next cycle and the recrystallisation liquors from the final cycle are recycled for reaction with DAED but the other acetic anhydride containing liquors obtained during the working up in the final cycle are run to waste.

8. A multicyclic process for making TAED which comprises, in each cycle, the step of reacting DAED with acetic anhydride, part at least of which is recovered from another cycle, and thereby forming a reaction mixture of TAED and acetic acid and anhydride and then distilling off acetic acid and working up the distillation residue to give substantially pure TAED, and in which the molar ratio of DAED:acetic anhydride in each cycle is at least 1:6 and wherein each cycle is carried out using the same volume of reaction mixture and in which the amount of DAED introduced into the reaction mixture in each cycle is less than in a preceding cycle.

9. A process according to claim 8 in which the said molar ratio of DAED:acetic anhydride in each cycle is below 1:10.

10. A process according to claim 8 in which the said molar ratio of DAED:acetic anhydride in each cycle is between 1:6.5 and 1:7.5.

11. A process according to claim 8 in which the said molar ratio of DAED:acetic anhydride in each cycle is about 1:7.0.

12. A process according to claim 8 in which the DAED is made by reacting EDA with acetic acid and the volume of reaction mixture in each cycle is constant and the amount of EDA introduced in each cycle is less than the amount introduced in a preceding cycle.

13. A process according to claim 8 in which the DAED is made by reacting EDA with acetic acid and the volume of reaction mixture in each cycle is constant and the amount of EDA introduced in second and subsequent cycles is 30 to 90% by weight of the amount introduced in the first cycle.

14. A multicyclic process for making TAED which comprises, in each cycle, the step of reacting DAED with acetic anhydride, part at least of which is recovered from another cycle, and thereby forming a reaction mixture of TAED and acetic acid and anhydride and then distilling off acetic acid and working up the distillation residue to give substantially pure TAED, wherein the molar ratio of DAED:acetic anhydride in each cycle is between 1:6.5 and 1:7.5, and wherein each cycle is carried out using the same volume of reaction mixture while the amount of DAED introduced into the reaction mixture in each cycle is less than in a preceding cycle.

15. A multicyclic process for making TAED which comprises, in each cycle, the step of reacting DAED with acetic anhydride, part at least of which is recovered from another cycle, and thereby forming a reaction mixture of TAED and acetic acid and anhydride and then distilling off acetic acid and working up the distillation residue to give substantially pure TAED, wherein the molar ratio of DAED:acetic anhydride in each cycle is between 1:6.5 and 1:7.5, and wherein the DAED is made by reacting EDA with acetic acid and the volume of reaction mixture in each cycle is constant while the amount of EDA introduced in each cycle is less than the amount introduced in a preceding cycle.

16. A process according to claim 15 in which the amount of EDA introduced in second and subsequent cycles is 30 to 90% by weight of the amount introduced in the first cycle.

17. A process according to claim 14 or claim 15 in which the said molar ratio of DAED:acetic anhydride in each cycle is about 1:7.0.

* * * * *